United States Patent
Grass et al.

(10) Patent No.: US 11,710,569 B2
(45) Date of Patent: Jul. 25, 2023

(54) CORONARY ARTERY DISEASE METRIC BASED ON ESTIMATION OF MYOCARDIAL MICROVASCULAR RESISTANCE FROM ECG SIGNAL

(71) Applicant: KONINKLIJKE PHILIPS N.V., Eindhoven (NL)

(72) Inventors: Michael Grass, Buchholz in der Nordheide (DE); Sven Prevrhal, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 793 days.

(21) Appl. No.: 16/500,207

(22) PCT Filed: Mar. 5, 2018

(86) PCT No.: PCT/EP2018/055367
§ 371 (c)(1),
(2) Date: Oct. 2, 2019

(87) PCT Pub. No.: WO2018/184779
PCT Pub. Date: Oct. 11, 2018

(65) Prior Publication Data
US 2021/0118569 A1      Apr. 22, 2021

Related U.S. Application Data

(60) Provisional application No. 62/482,223, filed on Apr. 6, 2017, provisional application No. 62/557,213, filed on Sep. 12, 2017.

(51) Int. Cl.
*G06K 9/00* (2022.01)
*G16H 50/30* (2018.01)
(Continued)

(52) U.S. Cl.
CPC ............. *G16H 50/30* (2018.01); *A61B 5/026* (2013.01); *A61B 5/319* (2021.01); *A61B 5/346* (2021.01);
(Continued)

(58) Field of Classification Search
None
See application file for complete search history.

(56) References Cited

U.S. PATENT DOCUMENTS 8,688,206 B2    4/2014  Gregg
9,757,073 B2    9/2017  Goshen
(Continued)

FOREIGN PATENT DOCUMENTS

WO    WO2016161308 A1    10/2016

OTHER PUBLICATIONS

PCT International Search Report, International application No. PCT/EP2018/055367, dated May 22, 2018.
(Continued)

*Primary Examiner* — Wei Wen Yang
(74) *Attorney, Agent, or Firm* — Larry Liberchuk

(57) ABSTRACT

A computing system (118) includes a computer readable storage medium (122) with computer executable instructions (124), including a biophysical simulator (126) and an electrocardiogram signal analyzer (128). The computing system further includes a processor (120) configured to execute the electrocardiogram signal analyzer determine myocardial infarction characteristics from an input electrocardiogram and to execute the biophysical simulator to simulate a fractional flow reserve or an instant wave-free ratio index from input cardiac image data and the determined myocardial infarction characteristics.

17 Claims, 5 Drawing Sheets

(51) Int. Cl.

| | | |
|---|---|---|
| *G06T 7/12* | (2017.01) | |
| *G16H 50/50* | (2018.01) | |
| *G16H 30/20* | (2018.01) | |
| *G16H 50/20* | (2018.01) | |
| *G16H 30/40* | (2018.01) | |
| *G06N 20/00* | (2019.01) | |
| *A61B 5/319* | (2021.01) | |
| *A61B 5/346* | (2021.01) | |
| *A61B 5/026* | (2006.01) | |
| *G06T 7/00* | (2017.01) | |
| *A61B 5/364* | (2021.01) | |
| *G16H 50/70* | (2018.01) | |
| *A61B 6/00* | (2006.01) | |

(52) U.S. Cl.
CPC ............ *A61B 5/364* (2021.01); *G06N 20/00* (2019.01); *G06T 7/0012* (2013.01); *G06T 7/12* (2017.01); *G16H 30/20* (2018.01); *G16H 30/40* (2018.01); *G16H 50/20* (2018.01); *G16H 50/50* (2018.01); *A61B 6/507* (2013.01); *A61B 6/5217* (2013.01); *G06T 2207/30048* (2013.01); *G06T 2207/30101* (2013.01); *G16H 50/70* (2018.01)

(56) References Cited

U.S. PATENT DOCUMENTS

| | | |
|---|---|---|
| 10,092,247 B2 | 10/2018 | Taylor |
| 10,140,700 B2 | 11/2018 | Takahashi |
| 10,162,932 B2 | 12/2018 | Sharma |
| 10,258,303 B2 | 4/2019 | Grass |
| 10,595,806 B2 | 3/2020 | Gilboa |
| 2004/0138574 A1 | 7/2004 | Groenwegen |
| 2006/0264770 A1 | 11/2006 | Wellens |
| 2012/0243761 A1 | 9/2012 | Senzig |
| 2013/0197884 A1 | 8/2013 | Mansi |
| 2015/0092999 A1 | 4/2015 | Schmitt |
| 2015/0324962 A1* | 11/2015 | Itu ............................. G06T 7/00 382/130 |
| 2018/0310888 A1* | 11/2018 | Itu .......................... G16H 50/50 |

OTHER PUBLICATIONS

Nickisch H. et al.,"Learning Patient-Specific Lumped Models for Interactive Coronary Blood Flow Simulations", Medical Image Computing and Computer-Assisted Intervention—MICCAI 2015: 18th International Conference, LNCS, vol. 9350, pp. 433-441, 2015.

Freiman M. et al., "Improving CCTA-Based Lesions' Hemodynamic Significance Assessment by Accounting for Partial Volume Modeling in Automatic Coronary Lumen Segmentation", Medical Physics, vol. 44, issue 3, pp. 1040-1049, 2017.

Zheng Y. et al., "Robust and Accurate Coronary Artery Centeriine Extraction in CTA by Combining Model-Driven and Data-Driven Approaches," Med Image Comput Assist Interv. 2013;16(Pt 3):74-81.

Ecabert O. et al., "Segmentation of the Heart and Great Vessels in CT Images Using a Model-Based Adaptation Framework," Medical Image Analysis, vol. 15, issue 6, Dec. 2011, pp. 863-876.

DeBruyne B. et al., "Fractional Flow Reserve in Patients with Prior Myocardial Infarction", Circulation, vol. 104, No. 2, pp. 157-162, Jul. 10, 2001.

* cited by examiner

CORONARY ARTERY DISEASE METRIC BASED ON ESTIMATION OF MYOCARDIAL MICROVASCULAR RESISTANCE FROM ECG SIGNAL

FIELD OF THE INVENTION

The following generally relates to a coronary artery disease metric and more particularly to a coronary artery disease metric based on an estimation of myocardial microvascular resistance from an electrocardiogram (ECG) signal, and is described with particular application to computed tomography (CT), but is also amenable to magnetic resonance (MR) angiography and/or other imaging modalities.

BACKGROUND OF THE INVENTION

The coronary arteries, which include a tree of vessels, normally deliver arterial blood and thus Oxygen to the heart muscle or myocardium via the microvascular structure connecting the coronary arteries with the myocardium. With coronary artery disease (CAD), lipid- and calcium-composited coronary plaque deposits block one or more of the vessels (stenosis). Stenosis can cause heart and chest pain (angina) and also acute myocardial infarction and brain stroke when plaque ruptures and blocks a downstream artery. Coronary microvascular dysfunction (CMD) may also play a role in cardiovascular disease, e.g., myocardial ischemia in patients with angina.

Coronary Computed Tomography Angiography (CCTA) is a non-invasive test to detect CAD in patients with chest pain and a gatekeeper technique to invasive Coronary Angiography (CA) in the Catheterization Lab. During CA, assessment of coronary function with an invasive pressure- or flow-sensor tipped catheter may be performed as well to gauge the functional impact of a stenosis in a fractional flow reserve (FFR) or instant wave-free ratio (iFR) measurement. Non-invasive techniques include simulating FFR and IFR based on CT data using computational fluid dynamics (CFD) and related computational methods (FFR-CT, iFR-CT). These techniques rely not only on the anatomical image data but also on boundary conditions of blood flow and pressure at the ostium, the proximal inlet of the coronary tree, and the tips of the coronary arteries.

The boundary conditions, generally, are assumed, including at the point at the tips where they become too thin to be faithfully extracted from the image data. A fundamental limitation of all the approaches is the fact that patient-specific boundary conditions need to be assigned using a generic model. Models typically involve externally measured blood pressure and the diameters of the arterial tips. Unfortunately, since these are determined mainly by the quality of the CT scan rather than actual patient anatomy, errors are introduced to the FFR-CT results that may lead to a wrong recommendation or diagnosis. A problem is that the resistance to blood flow transitioning from the coronaries into the myocardial microvascular structure is not taken into account, and this is exacerbated by the prevalence of CMD, and microvascular resistance is not available to direct measurement.

SUMMARY OF THE INVENTION

Aspects described herein address the above-referenced problems and others.

In one aspect, a computing system includes a computer readable storage medium with computer executable instructions, including a biophysical simulator and an electrocardiogram signal analyzer. The computing system further includes a processor configured to execute the electrocardiogram signal analyzer determine myocardial infarction characteristics from an input electrocardiogram and to execute the biophysical simulator to simulate a fractional flow reserve or an instant wave-free ratio index from input cardiac image data and the determined myocardial infarction characteristics.

In another aspect, a computer readable storage medium is encoded with computer readable instructions, which, when executed by a processor of a computing system, causes the processor to receive cardiac image data, receive an electrocardiogram signal, and simulate a fractional flow reserve or an instant wave-free ratio index from the cardiac image data and myocardial infarction characteristics of the electrocardiogram signal, wherein the determined myocardial infarction characteristics include an estimate of one or more of an existence of a myocardial infarction, a position of the myocardial infarction, and a size of the myocardial infarction.

In another aspect, a method includes receiving cardiac image data, receiving an electrocardiogram signal, and simulating a fractional flow reserve or an instant wave-free ratio index from the cardiac image data and myocardial infarction characteristics of the electrocardiogram signal, wherein the myocardial infarction characteristics include an estimate of one or more of an existence of a myocardial infarction, a position of the myocardial infarction, and a size of the myocardial infarction.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
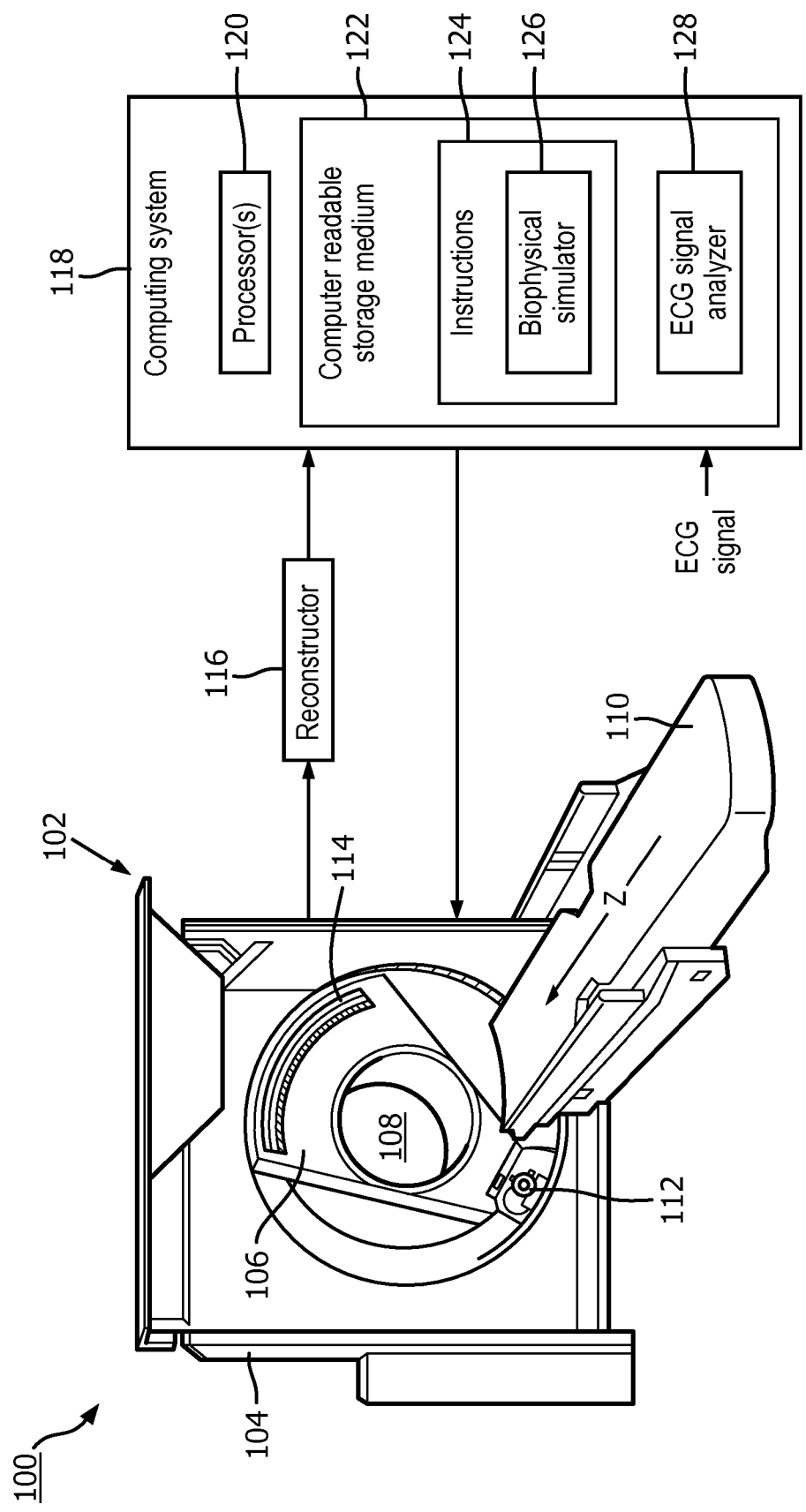
FIG. 1 schematically illustrates an example system with a computing system, which includes a biophysical simulator and an ECG signal analyzer, and an imaging system.

FIG. 1 schematically illustrates a system 100 including an imaging system 102 such as a CT scanner. In a variation, the imaging system 100 includes an MR scanner. The illustrated imaging system 102 includes a generally stationary gantry 104 and a rotating gantry 106, which is rotatably supported by the stationary gantry 104 and rotates around an examination region 108 about a z-axis. A subject support 110, such as a couch, supports an object or subject in the examination region 108.

A radiation source 112, such as an x-ray tube, is rotatably supported by the rotating gantry 106, rotates with the rotating gantry 106, and emits radiation that traverses the examination region 108. A radiation sensitive detector array 114 subtends an angular arc opposite the radiation source 112 across the examination region 1088. The array 114 detects radiation traversing the examination region 108 and generates an electrical signal(s) (projection data) indicative thereof. A reconstructor 116 reconstructs the projection data, generating volumetric image data indicative of the examination region 108.

The system 100 further includes a computing system 118, which, in this example, serves as an operator console. The console 118 includes a processor 120 (e.g., a microprocessor, a central processing unit, etc.) and a computer readable storage medium 122, which excludes transitory medium, and includes non-transitory medium such as a physical memory device, etc. The console 118 further includes a human readable output device(s) such as a display monitor, and an input device(s) such as a keyboard, mouse, etc.

The computer readable storage medium 122 includes instructions 124 for a biophysical simulator 126 and an electrocardiogram (ECG, or EKG) analyzer 128. The processor 120 is configured to execute the instructions 124 and/or software that allows the operator to interact with and/or operate the scanner 102 via a graphical user interface (GUI) or otherwise. The processor 120 may additionally, or alternatively, execute a computer readable instruction(s) carried by a carrier wave, a signal and/or other transitory medium.

In a variation, the biophysical simulator 126 and the ECG analyzer 128 are part of another computing system, which is separate from the console 118 and the system 100. In this instance, the other computing system is similar to the console 118 in that it includes a processor, computer readable storage medium, an input device, and an output device, but it does not include the software that allows the operator to interact with and/or operate the scanner 102.

The ECG analyzer 128 receives, an input, an ECG signal of a patient under evaluation. The ECG signal can be acquired concurrently with scanning a patient, before scanning the patient and/or after scanning the patient. In one instance, the ECG signal includes a 12-lead ECG signal. Alternatively, or additionally, the ECG signal includes a 3-lead, 5-lead, a more than 12-lead, etc. ECG signal. Alternatively, or additionally, the ECG signal is determined from a cardiac mapping using a vest of electrodes, such as the ECVUE vest, a product of CardioInsight, Ohio, USA. The ECG analyzer 128 analyzes the ECG signal and estimates an existence, a position and/or a size of a myocardial infarction (MI) therefrom, as described in detail below.

The biophysical simulator 126 is configured to process the volumetric image data and the ECG estimates and perform a biophysical simulation. With respect to FFR, the biophysical simulator determines the index based on CCTA image data. In one instance, this includes using CCTA image data to derive a geometrical model of the coronary tree and determine boundary conditions therefrom for the simulation. As described in detail below, the biophysical simulator 126 adjusts the boundary conditions (e.g., microvascular resistance) based on the ECG estimates and/or first integrates the ECG estimates into the CCTA image data. By taking into account the ECG signal, the biophysical simulator 126 can provide a more accurate index (e.g., less error introduced by assumptions, models, image quality, etc.), relative to a configuration which does not consider this information.

Figure 2:
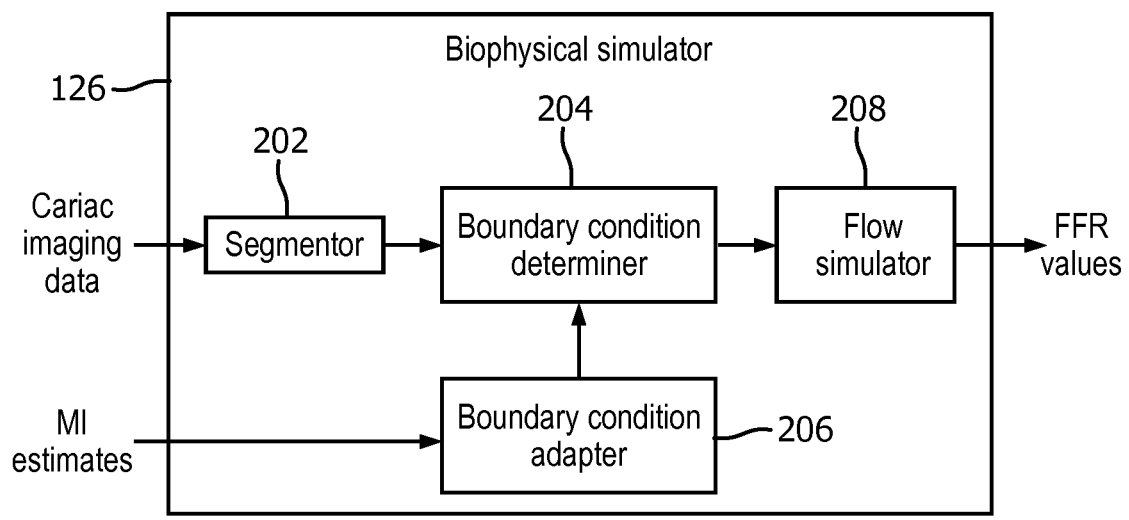
FIG. 2 schematically illustrates an example of the biophysical simulator.

FIG. 2 schematically illustrates an example of the biophysical simulator 126. In this example, the biophysical simulator 126 includes a segmentor 202, a boundary condition determiner 204, a boundary condition adapter 206, and a flow simulator 208. The biophysical simulator 126 receives, as input, CCTA image data from the imaging system 100, a data repository (e.g., a radiology information system (RIS), a picture and archiving system (PACS), etc.), and/or other apparatus. The biophysical simulator 126 also receives, as input, the MI estimates (of the existence, the position, the size, etc. of an infarct) from the ECG analyzer 128.

Figure 3:
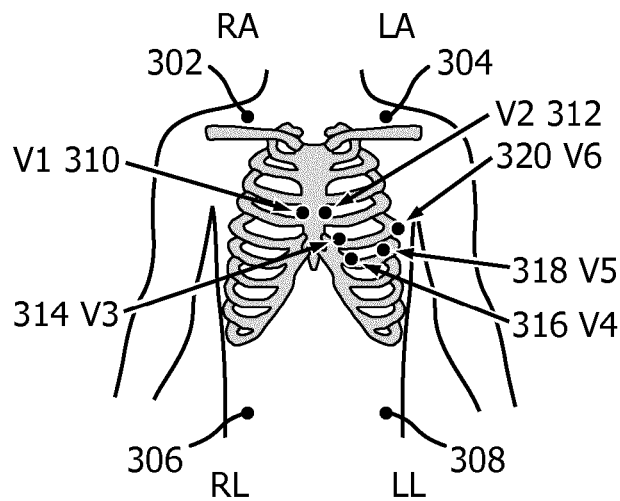
FIG. 3 schematically illustrates example placement of electrodes for a 12-lead ECG.

Briefly turning to FIG. 3, an example of approximate electrode placement of the ten electrodes for a 12-lead ECG is schematically illustrated. The electrodes include a right arm (RA) electrode 302, a left arm (LA) electrode 304, a right leg (RL) electrode 306, a left leg (LG) electrode 308, a V1 electrode 310 in the fourth intercostal space (between ribs 4 and 5) just to the right of the sternum (breastbone), a V2 electrode 312 in the fourth intercostal space (between ribs 4 and 5) just to the left of the sternum, a V3 electrode 314 over rib 5, a V4 electrode 316 in the fifth intercostal space (between ribs 5 and 6) in the mid-clavicular line, a V5 electrode 318 horizontally even with V4, in the left anterior axillary line, and a V6 electrode 320 horizontally even with V4 and V5 in the midaxillary line.

The 12 leads are: I, II, III, aVR, aVL, aVF, V1, V2, V3, V4, V5 and V6. Lead I is a voltage between the electrode 304 and electrode 302 (I=LA−RA). Lead II is a voltage between the electrode 308 and the electrode 306 (II=LL−RA). Lead III is a voltage between the electrode 308 and the electrode 304 (III=LL−LA). Lead aVR is a voltage between the electrode 302 and a combination of the electrode 304 and the electrode 308 (aVR=RA−½(LA+LL)). Lead aVL is a voltage between the electrode 304 and a combination of the electrode 302 and the electrode 308 (aVL=LA−½(RA+LL). Lead aVF is a voltage between the electrode 308 and a combination of the electrode 302 and the electrode 304 (aVF=LL−½(RA+LA).

Figure 4:
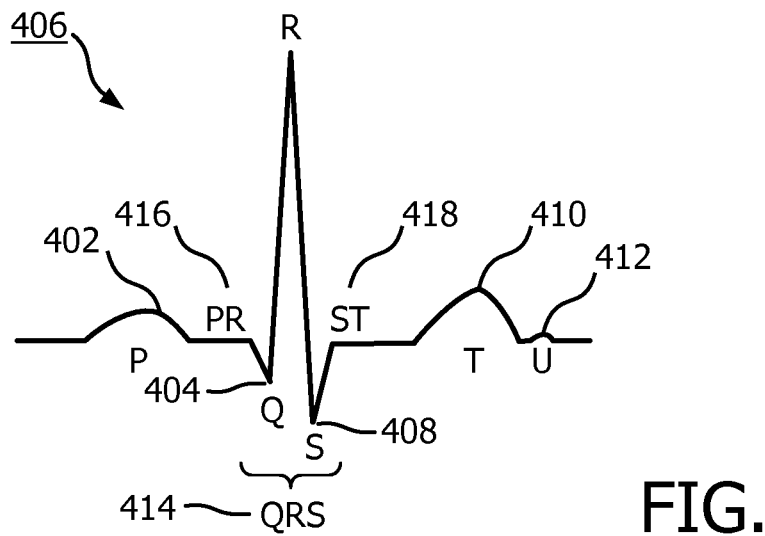
FIG. 4 schematically illustrates an example "normal" ECG signal.

FIG. 4 schematically illustrates an example of an ECG signal 400 in "normal" sinus rhythm. The signal 400 includes a P wave 402, a Q wave 404, an R wave 406, an S wave 408, a T wave 410, and a U wave 412. The Q, R and S waves for a QRS complex 414. The P wave 402 represents atrial depolarization, the QRS complex 414 represents ventricular depolarization, the T wave 410 represents ventricular repolarization, and the U wave 412 represents papillary muscle repolarization. A PR interval 416 is the interval from the beginning of the P wave 402 to the beginning of the QRS complex 414. An ST segment 418 connects the QRS complex 414 and the T wave 410, and represents the period when the ventricles are depolarized.

With reference to FIGS. 1-4, the ECG analyzer 128 analyzes the ECG signal and estimates an existence of a myocardial infarction (MI) therefrom. In one instance, the ECG analyzer 128 achieves this by analyzing one or more of the waves 402-412. For example, the ECG analyzer 128 can analyze the ST segment 418, where a depressed or elevated ST segment 418 may indicate an MI. In another example, the ECG analyzer 128 can analyze the T wave 410, where an inverted T wave 410 may indicate an MI. This data can be analyzed for a patient through a comparison with a previously acquired and known normal ECG signal of the patient, through a comparison with a model normal and/or abnormal ECG signal, through a comparison of known normal and/or abnormal ECG signals from a population of patients, etc.

Additionally, or alternatively, the ECG analyzer 128 estimates a position of the MI. For this, the ECG analyzer 128 can use the leads V1 to V4, which measure electrical activity from the front of the heart, which is supplied by the left anterior descending coronary artery (LAD), to estimates an MI in an anterior region of the heart. The ECG analyzer 128 can use the leads I, aVL, V5 and V6, which measure electrical activity from the left of the heart, which is supplied by the left circumflex coronary artery (LC), to estimates an MI in a lateral region of the heart. The ECG analyzer 128 can use the II, III and aVF, which measure electrical activity from under the heart, which is supplied by the right coronary artery (RCA), to estimates an MI in an inferior region of the heart.

Additionally, or alternatively, the ECG analyzer 128 estimates a size of the MI. For example, MI size can be estimated by ECG signal characteristics such as a deepened Q wave, reduced R-wave amplitude, elevated ST segments and/or inverted T wave on various leads. The ECG analyzer 128 can estimates any or all of these characteristics. Furthermore, the ECG analyzer 128 can analyze characteristics as described in U.S. Pat. No. 8,688,206 B2, entitled "Visualization of myocardial infarct size in diagnostic ECG," and filed on Apr. 25, 2011, the entirety of which is incorporated herein by reference. Additionally, or alternatively, a clinician may visually analyze the ECG signal and provide additional information to the ECG analyzer 128, which can use this information to estimate an MI.

Figure 10:
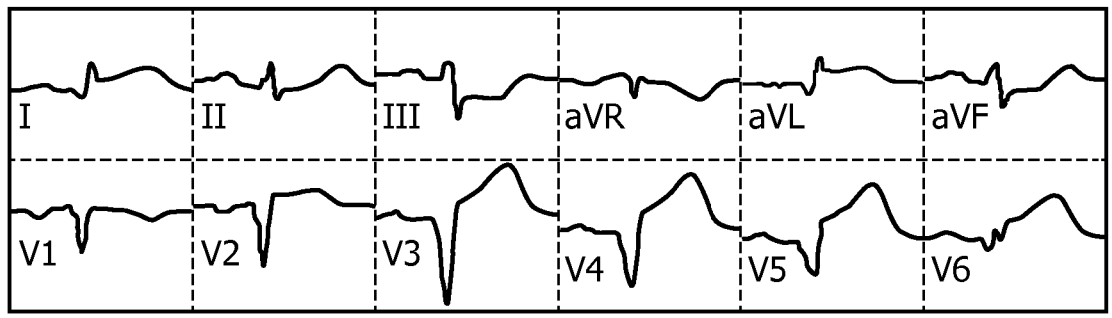
FIG. 10 shows an example ECG signal indicating an infarct.
Figure 11:
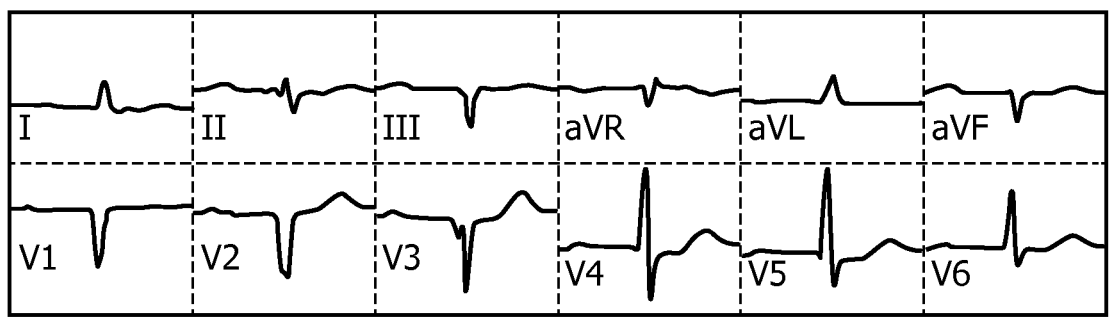
FIG. 11 shows another example ECG signal indicating a different type of infarct.
Figure 12:
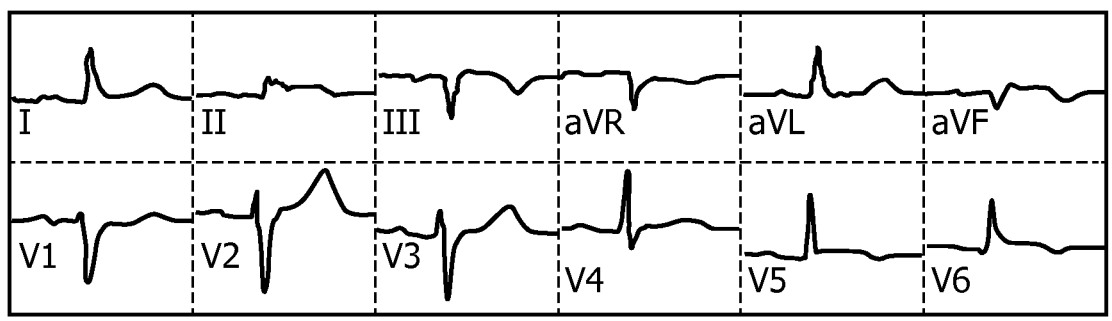
FIG. 12 shows yet another example ECG signal indicating yet another type of infarct.
Figure 13:
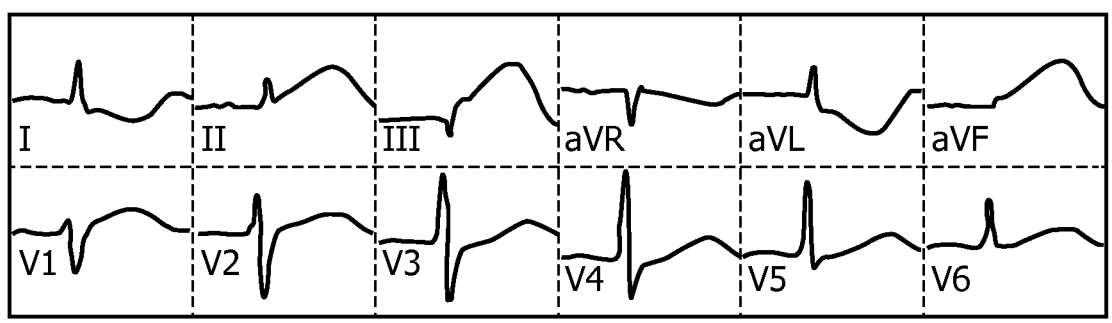
FIG. 13 shows still another example ECG signal indicating still another type of infarct.

Generally, all of the waves of the ECG signal and the intervals between them may have a predictable time duration, a range of acceptable amplitudes (voltages), and a typical morphology. The ECG analyzer 128 can use any deviation from the normal tracing to estimate an MI. FIGS. 10, 11, 12 and 13 show example ECG signals with deviations from the "normal" ECG signal shown in FIG. 4. FIG. 10 shows an ECG signal indicating a Stage I extended front apical infarction. FIG. 11 shows an ECG signal indicating a Stage III anteroseptal infarction. FIG. 12 shows an ECG signal indicating an intermediate stage posterolateral infarction. FIG. 13 shows an ECG signal indicating a Stage I rear wall infarction.

Figures 5, 6:
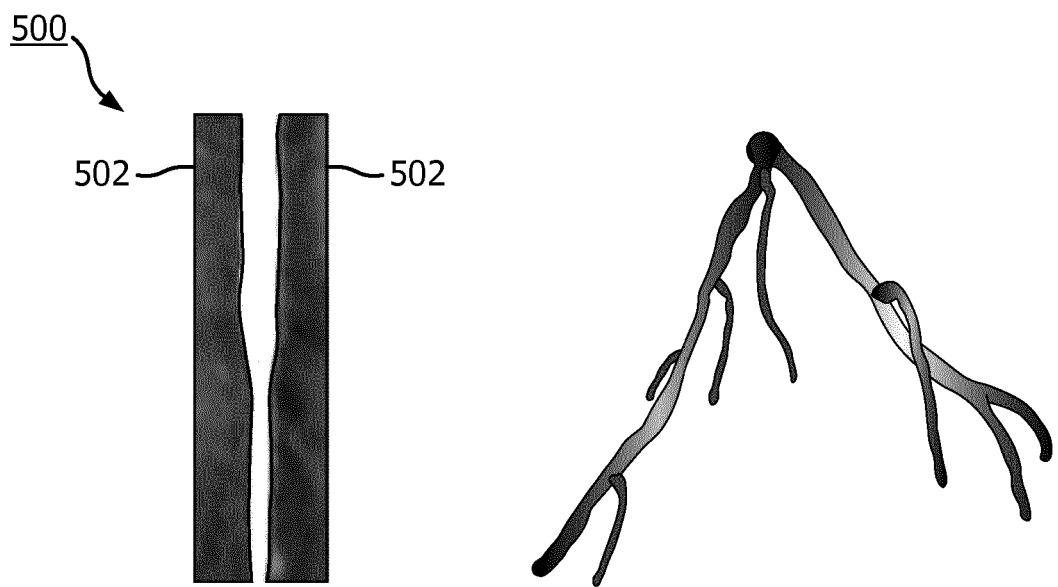
FIG. 5 illustrates an example segmentation of the coronary arteries.
FIG. 6 illustrates an example anatomical model of the coronary arteries.

With reference to FIGS. 1 and 2, the segmentor 202 employs a segmentation algorithm to segment the coronary tree from the CCTA imaging data. The segmentation can be performed automatically (e.g., machine learning, etc.) or semi-automatically (e.g., with user assistance). In one instance, the segmentation includes identifying and/or extracting coronary artery centerlines and/or lumen geometry (e.g., diameter, perimeter, cross-sectional area, etc.) therefrom. The segmentation can be based on voxel intensity, object shape, and/or other characteristics. FIG. 5 shows segmentation of a portion 500 of an individual vessel showing opposing walls 502 of the vessel lumen, and FIG. 6 shows a segmented coronary tree 600.

Examples of suitable approaches for extracting a coronary tree from CCTA imaging data are discussed in Zheng et al., "Robust and accurate coronary artery centerline extraction in CTA by combining model-driven and data-driven approaches," Med Image Comput Assist Interv. 2013; 16(Pt 3):74-81, Ecabert et al., "Segmentation of the heart and great vessels in CT images using a model-based adaptation framework," Med Image Anal. 2011 December; 15(6):863-76, and Freiman et al., "Improving CCTA-based lesions' hemodynamic significance assessment by accounting for partial volume modeling in automatic coronary lumen segmentation," Med Phys. 2017 March; 44(3):1040-1049. Other approaches are also contemplated herein.

The boundary condition determiner 204 determines boundary conditions for a computational fluid dynamic simulation of blood flow in vessels from the user adjusted coronary tree segmentation and/or the segmentor 202 adapted user adjusted coronary tree segmentation. With one approach, a parametric lumped model is employed. The model includes a centerline representation using nonlinear resistances, with elements indicating inflow and outflow boundary conditions, and elements representing tree segment transfer functions, which include a series of linear and nonlinear resistance elements reflecting vessel geometry (e.g., diameter, perimeter, cross-sectional area, etc.) and/or hydraulic effects.

An example of a lumped model is discussed in Nickisch, et al., "Learning Patient-Specific Lumped Models for Interactive Coronary Blood Flow Simulations," in Medical Image Computing and Computer-Assisted Intervention—MICCAI 2015: 18th International Conference, LNCS, Vol. 9350, 2015, vol. 9350, pp. 433-441. An example of deriving boundary conditions is described in EP14174891.3, filed Jun. 30, 2014, and entitled "Enhanced Patient's Specific Modelling For FFR-CT," which is incorporated herein by reference in its entirety. Other approaches are also contemplated herein.

The boundary condition adapter 206 is configured to adapt the boundary conditions. For example, where the MI estimates indicate an infarction of the cardiac tissue supplied by the LAD (and/or the LC, the RCA, etc.), the boundary condition adapter 206 can increase the myocardial vascular resistance (MVR) boundary conditions (e.g., $R_a=R_i+\Delta R$, where $R_a$=adapted resistance, $R_o$=initial resistance, and $\Delta R$ is the increase) for the LAD (and/or the LC, the RCA, etc.) to reflect an increase in MVR due to muscle cell damage and/or death that incurred during the infarct. The amount of change ($\Delta R$) of the boundary conditions can be estimated from data known from cardiac physiology. For example, in Cardiac CT and MR, late enhancement describes the delayed myocardial influx of contrast media typically seen in post-ischemic myocardial infarction scar tissue and caused by the altered microcirculatory resistance in subendocardial tissue layer. Alternatively, or additionally, where a lumped parameter model is used and measured FFR (and/or iFR) data with known ECG modifications according to myocardial infarction is available, the model can be trained against data, and the boundary conditions can be trained such that the calculated and measured FFR (and/or iFR) data match.

Figure 7:
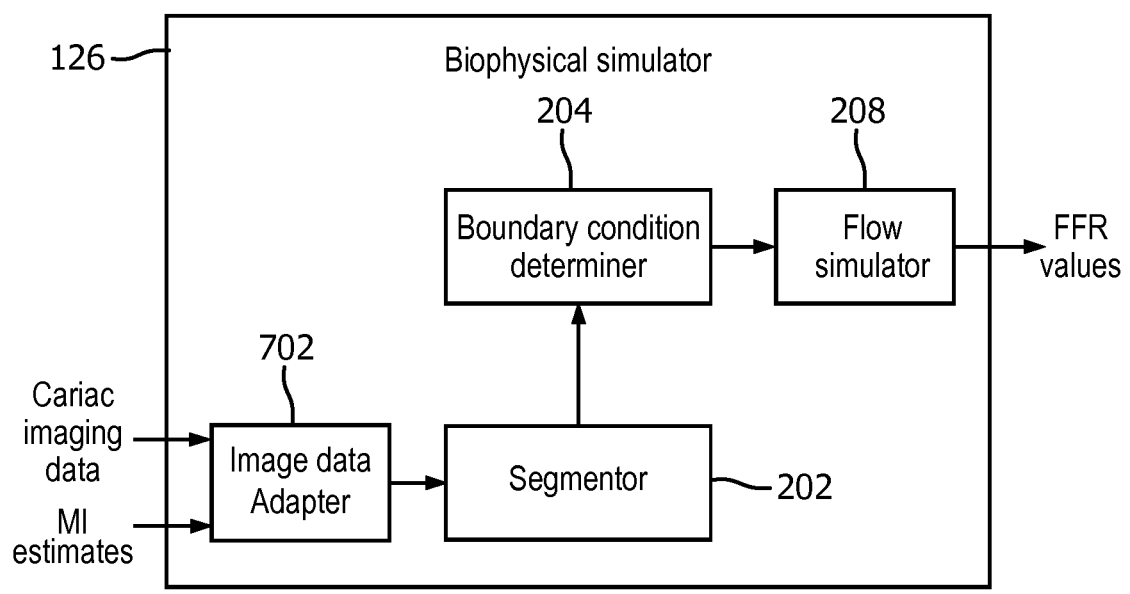
FIG. 7 schematically illustrates another example of the biophysical simulator.

The flow simulator 210 performs a flow simulation with the boundary conditions and generates and outputs FFR values. Flow simulations can be done, e.g., using a computational fluid dynamics (CFD) approach and/or other approach. Examples of computing FFR values are described in US 2015/0092999 A1, filed May 10, 2013, and entitled "Determination of a fractional flow reserve (FFR) value for a stenosis of a vessel," US 2015/0282765 A1, filed Oct. 24, 2013, and entitled "Fractional flow reserve (FFR) index," which are incorporated herein by reference in their entireties. The FFR index can be displayed via a display monitor, stored, conveyed to another device, etc. In General, FIG. 7 schematically illustrates a variation in which the biophysical simulator 126 includes an image data adapter 702 configured to integrate the MI estimates into spatial coordinates of the cardiac image data. In this example, the biophysical simulator 126 does not include boundary condition adapter 206. In a variation, the biophysical simulator 126 includes both the boundary condition adapter 206 and the image data adapter 702.

In one instance, the image data adapter 702 integrates the ECG estimates into the CCTA image data. This can be achieved via a personalized cardiac shape model, for example by inferring the coronary arteries associated with the involved cardiac feeding territory or territories and/or otherwise. The biophysical simulator 126 then processes the image data as described herein with the segmentor 202, the boundary condition determiner 204, and the flow simulator 208. In this instance, the boundary conditions reflect the MI estimates, which were integrated with the image data prior to boundary condition determination.

In another variation, the approaches described in connection with FIGS. 2 and 7 can be combined with invasive catheter measurements, which may deliver improved quantitative data of coronary flow.

FIGS. 1, 2 and 7 described example that use FFR as a measure of a functional significance of coronary artery disease. In a variation, the approach described herein can also be applied to instantaneous wave-free ratio (iFR) and/or other measures. Generally, iFR is performed using pressure wires that are passed distal to the coronary stenosis and isolates a specific period in diastole, called the wave-free period, and computes a ratio of distal coronary pressure to a pressure observed in the aorta over this period.

Figure 8:
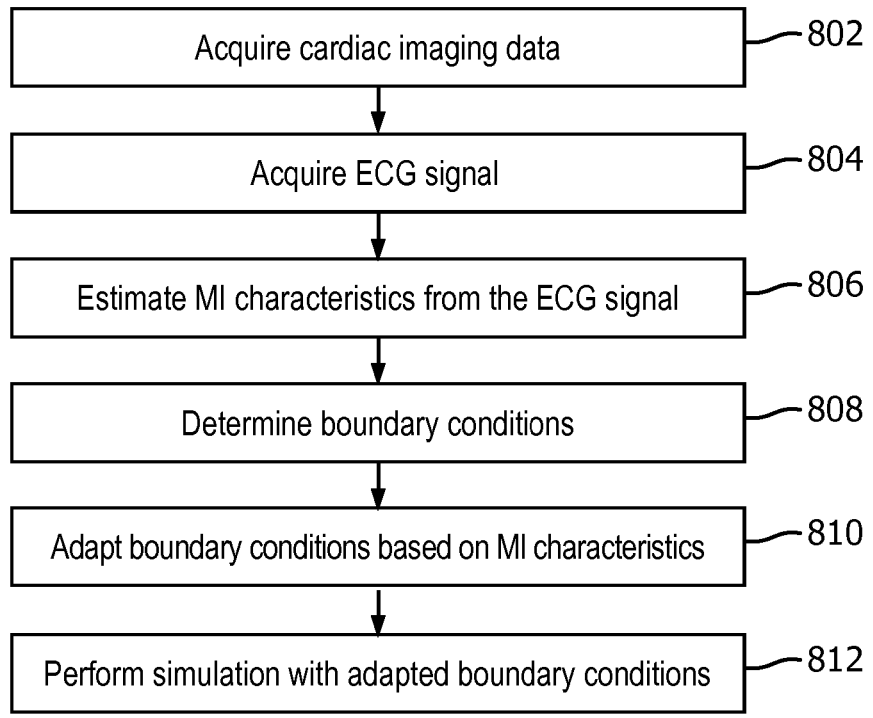
FIG. 8 illustrates an example method in accordance with an embodiment herein.

FIG. 8 illustrates an example method in accordance with an embodiment described herein.

It is to be appreciated that the ordering of the acts is not limiting. As such, other orderings are contemplated herein. In addition, one or more acts may be omitted and/or one or more additional acts may be included.

At 802, cardiac imaging data is acquired, as described herein and/or otherwise.

At 804, an ECG signal is acquired, as described herein and/or otherwise.

At 806, characteristics (e.g., an existence, a position, a size, etc.) of an MI is determined from the ECG signal, as described herein and/or otherwise.

At 808, boundary conditions are determined from the image data, as described herein and/or otherwise.

At 810, the boundary conditions are adapted based on the MI characteristics, as described herein and/or otherwise.

At 812, the coronary function is assessed using the adapted boundary conditions, as described herein and/or otherwise.

The above may be implemented by way of computer readable instructions, encoded or embedded on computer readable storage medium, which, when executed by a computer processor(s), cause the processor(s) to carry out the described acts. Additionally, or alternatively, at least one of the computer readable instructions is carried by a signal, carrier wave or other transitory medium, which is not computer readable storage medium.

Figure 9:
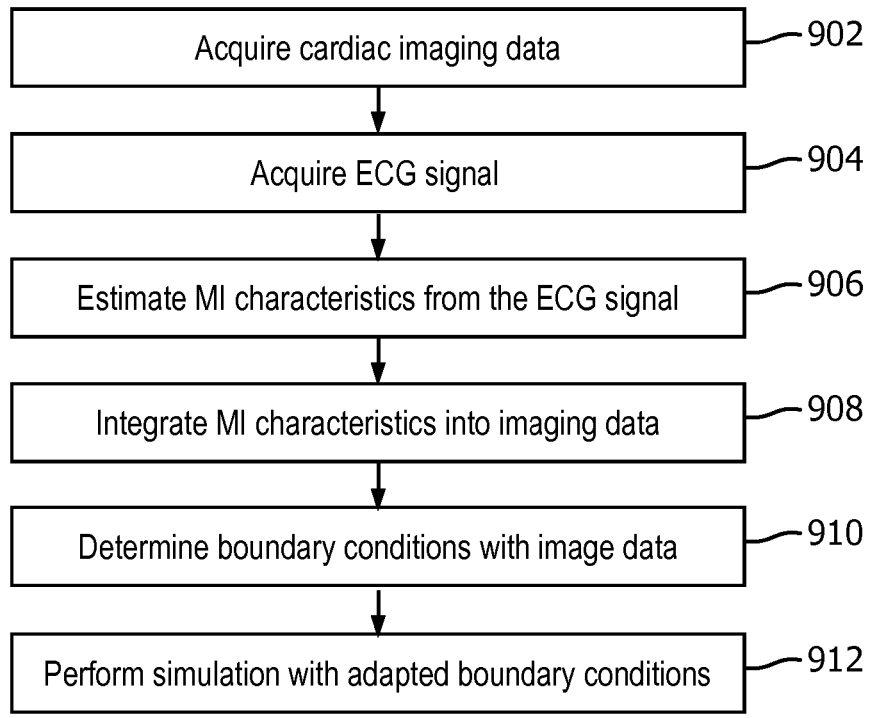
FIG. 9 illustrates another example method in accordance with an embodiment herein.

FIG. 9 illustrates an example method in accordance with an embodiment described herein.

It is to be appreciated that the ordering of the acts is not limiting. As such, other orderings are contemplated herein. In addition, one or more acts may be omitted and/or one or more additional acts may be included.

At 902, cardiac imaging data is acquired, as described herein and/or otherwise.

At 904, an ECG signal is acquired, as described herein and/or otherwise.

At 906, characteristics (e.g., an existence, a position, a size, etc.) of an MI is determined from the ECG signal, as described herein and/or otherwise.

At 908, the MI characteristics are integrated with the image data, as described herein and/or otherwise.

At 910, boundary conditions are determined from the image data integrated with the MI characteristics, as described herein and/or otherwise.

At 912, the coronary function is assessed using the adapted boundary conditions, as described herein and/or otherwise.

The above may be implemented by way of computer readable instructions, encoded or embedded on computer readable storage medium, which, when executed by a computer processor(s), cause the processor(s) to carry out the described acts. Additionally, or alternatively, at least one of the computer readable instructions is carried by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computing system, comprising:
   a computer readable storage medium with computer executable instructions; and
   a processor configured to execute the instructions to:
   receive cardiac image data;
   receive an electrocardiogram signal;
   determine myocardial infarction characteristics from the electrocardiogram signal;
   simulate a fractional flow reserve index or an instant wave-free ratio index from the cardiac image data and the myocardial infarction characteristics,
   wherein the myocardial infarction characteristics include an electrocardiogram estimate that includes an estimate of one or more of an existence of a myocardial infarction, a position of the myocardial infarction, and a size of the myocardial infarction; and adapt boundary conditions based on the electrocardiogram estimate.

2. The system of claim 1, wherein the processor is further configure to determine the boundary conditions from a coronary tree segmented from the cardiac image data, and adapt the boundary conditions with the myocardial infarction characteristics.

3. The system of claim 2, wherein the adaption includes changing a microvascular resistance of an element of a model of coronary arteries.

4. The system of claim 2, wherein the adaption includes increasing a microvascular resistance of coronary arteries of a model.

5. The system of claim 2, wherein the adaption is estimated from cardiac physiology.

6. The system of claim 2, wherein the boundary conditions are adapted through training with a fractional flow reserve measurement or an instant wave-free ratio measurement such that the fractional flow reserve index or the instant wave-free ratio index matches the fractional flow reserve measurement or the instant wave-free ratio measurement.

7. The system of claim 1, wherein the processor is further configured to integrate the determined myocardial infarction characteristics into the cardiac image data.

8. The system of claim 7, wherein the processor integrates the myocardial infarction characteristics into spatial coordinates of the cardiac image data using a personalized cardiac shape model.

9. The system of claim 7, wherein the processor is further configured to determine the boundary conditions from the image data integrated with the myocardial infarction characteristics and determine the fractional flow reserve index therefrom.

10. A non-transitory computer readable storage medium encoded with computer readable instructions which, when executed by a processor, cause the processor to perform a method comprising:

receiving cardiac image data;
receiving an electrocardiogram signal;
determining myocardial infarction characteristics from the electrocardiogram signal;
simulating a fractional flow reserve index or an instant wave-free ratio index from the cardiac image data and the myocardial infarction characteristics, wherein the myocardial infarction characteristics include an electrocardiogram estimate that includes an estimate of one or more of an existence of a myocardial infarction, a position of the myocardial infarction, and a size of the myocardial infarction; and
adapting boundary conditions based on the electrocardiogram estimate.

11. The non-transitory computer readable storage medium of claim 10, wherein the processor determines the boundary conditions from a coronary tree segmented from the cardiac image data, adapts the boundary conditions with the myocardial infarction characteristics, and simulates the fractional flow reserve index or the instant wave-free ratio index with the adapted boundary conditions.

12. The non-transitory computer readable storage medium of claim 10, wherein the processor integrates the myocardial infarction characteristics into spatial coordinates of the input cardiac image data and simulates the fractional flow reserve index or the instant wave-free ratio index with the integrated cardiac image data.

13. The non-transitory computer readable storage medium of claim 10, wherein the processor employs a training algorithm and one of a fractional flow reserve measurement or an instant wave-free ratio measurement to simulate a fractional flow reserve index or an instant wave-free ratio index that matches the fractional flow reserve measurement or the instant wave-free ratio measurement.

14. A method, comprising:
receiving cardiac image data;
receiving an electrocardiogram signal;
determining myocardial infarction characteristics from the electrocardiogram signal;
simulating a fractional flow reserve index or an instant wave-free ratio index from the cardiac image data and the myocardial infarction characteristics, wherein the myocardial infarction characteristics include an electrocardiogram estimate that includes an estimate of one or more of an existence of a myocardial infarction, a position of the myocardial infarction, and a size of the myocardial infarction; and
adapting boundary conditions based on the electrocardiogram estimate.

15. The method of claim 14, further comprising:
segmenting a coronary tree from the cardiac image data;
determining the boundary conditions from the segmented cardiac image data;
adapting the boundary conditions with the myocardial infarction characteristics; and
simulating the fractional flow reserve index or the instant wave-free ratio index with the adapted boundary conditions.

16. The method of claim 15, further comprising:
integrating the myocardial infarction characteristics into spatial coordinates of the cardiac image data;
segmenting the coronary tree from the cardiac image data integrated with the myocardial infarction characteristics;
determining the boundary conditions from the segmented cardiac image data; and
simulating the fractional flow reserve index or the instant wave-free ratio index with the boundary conditions.

17. The method of claim 16, further comprising:
segmenting the coronary tree from the cardiac image data;
receiving one of a fractional flow reserve measurement index and an instant wave-free ratio measurement index;
determining boundary conditions from the segmented cardiac image data and one of the fractional flow reserve measurement index and the instant wave-free ratio measurement index such that the simulated fractional flow reserve index or the simulated instant wave-free ratio index matches the fractional flow reserve measurement index or the instant wave-free ratio measurement index, respectively; and
simulating the fractional flow reserve index or the instant wave-free ratio index with the boundary conditions.

* * * * *